US011376426B2

(12) United States Patent
Gimelli et al.

(10) Patent No.: US 11,376,426 B2
(45) Date of Patent: Jul. 5, 2022

(54) HAND-HELD DEVICE FOR ELECTRICALLY POWERED SKIN TREATMENT

(71) Applicant: Swiss Spa System Ltd., Hong Kong (CN)

(72) Inventors: Bruno Gimelli, Zollikofen (CH); James N. Doyle, Jr., Ft. Myers, FL (US)

(73) Assignee: Swiss Spa System Ltd., Hong Kong (CN)

( * ) Notice: Subject to any disclaimer, the term of this patent is extended or adjusted under 35 U.S.C. 154(b) by 938 days.

(21) Appl. No.: 16/158,037

(22) Filed: Oct. 11, 2018

(65) Prior Publication Data

US 2019/0038896 A1 Feb. 7, 2019

Related U.S. Application Data

(62) Division of application No. 14/372,433, filed as application No. PCT/EP2013/000112 on Jan. 16, 2013, now Pat. No. 10,124,165.

(30) Foreign Application Priority Data

Jan. 16, 2012 (DE) ...................... 10 2012 000 563.6
May 14, 2012 (DE) ...................... 10 2012 009 514.7

(51) Int. Cl.
*A61N 1/32* (2006.01)
*A61H 23/00* (2006.01)
(Continued)

(52) U.S. Cl.
CPC ............. *A61N 1/328* (2013.01); *A61H 7/002* (2013.01); *A61H 7/005* (2013.01); *A61H 23/00* (2013.01);
(Continued)

(58) Field of Classification Search
CPC ........ A61H 7/001; A61H 7/003; A61H 7/004; A61H 7/005; A61H 23/00; A61H 23/02;
(Continued)

(56) References Cited

U.S. PATENT DOCUMENTS

| 5,279,284 A | 1/1994 | Fenn | A61H 23/0218 |
| | | | 601/108 |
| 5,607,461 A * | 3/1997 | Lathrop | A61N 1/326 |
| | | | 607/75 |

(Continued)

FOREIGN PATENT DOCUMENTS

| EP | 2 277 585 A2 | 1/2011 |
| EP | 2 384 707 A1 | 11/2011 |
| WO | WO 2005/087308 A1 | 9/2005 |

OTHER PUBLICATIONS

German Search Report dated Jan. 21, 2013, with English translation (Eleven (11) pages).

*Primary Examiner* — Michael J Tsai
(74) *Attorney, Agent, or Firm* — Crowell & Moring LLP

(57) ABSTRACT

A hand-held device for electrically powered skin treatment includes a housing which is adapted to be grasped by a hand of a user, a first outer electrode which is adapted to be in contact with the hand of the user when the device is held in the hand of the user for use, a second outer electrode disposed on a side of the housing where the second outer electrode is placeable on an area of skin to be treated, and an electrically operated vibrator where the electrically operated vibrator is fixed by a socket on a side wall of the housing and is adapted to vibrate the side wall together with the second outer electrode when operated so that during operation of the device, the device produces an intensified massaging effect on the area of skin to be treated.

7 Claims, 12 Drawing Sheets

(51) Int. Cl.
*A61N 1/04* (2006.01)
*A61H 23/02* (2006.01)
*A61H 7/00* (2006.01)

(52) U.S. Cl.
CPC ....... *A61H 23/0263* (2013.01); *A61N 1/0412* (2013.01); *A61N 1/0428* (2013.01); *A61N 1/0472* (2013.01); *A61N 1/0476* (2013.01); *A61N 1/322* (2013.01); *A61N 1/325* (2013.01); *A61N 1/327* (2013.01); *A61H 2201/0153* (2013.01); *A61H 2201/10* (2013.01); *A61H 2201/105* (2013.01); *A61H 2201/1215* (2013.01); *A61H 2201/1253* (2013.01); *A61H 2201/1418* (2013.01); *A61H 2201/1654* (2013.01); *A61H 2201/1669* (2013.01); *A61H 2201/1695* (2013.01); *A61H 2201/50* (2013.01); *A61H 2201/5023* (2013.01)

(58) Field of Classification Search
CPC ............ A61H 23/0254; A61H 23/0263; A61H 2201/10; A61H 2201/5028; A61H 2201/5025
See application file for complete search history.

(56) References Cited

U.S. PATENT DOCUMENTS

| | | | |
|---|---|---|---|
| 5,925,002 A | 7/1999 | Wollman | A61H 23/0263 601/46 |
| 6,119,038 A | 9/2000 | Cook | |
| 6,385,487 B1 | 5/2002 | Henley | |
| 6,443,915 B1* | 9/2002 | Hwang | A61N 1/32 601/15 |
| 7,083,580 B2 | 8/2006 | Bernabei | A61H 7/008 601/15 |
| 7,228,184 B2* | 6/2007 | Heath | A61P 31/12 607/68 |
| 2003/0171702 A1* | 9/2003 | Thompson | A45D 34/04 601/72 |
| 2004/0073274 A1* | 4/2004 | Cook | A61N 1/328 607/50 |
| 2004/0236255 A1* | 11/2004 | Cook | A61N 1/328 601/15 |
| 2005/0107832 A1* | 5/2005 | Bernabei | A61H 23/02 607/3 |
| 2005/0234516 A1* | 10/2005 | Gueret | A61N 1/328 607/3 |
| 2007/0247793 A1 | 10/2007 | Carnevali | G06F 1/1625 361/679.1 |
| 2008/0183251 A1 | 7/2008 | Azar | A61B 18/18 607/101 |
| 2009/0318853 A1 | 12/2009 | Reed | A61M 35/003 604/22 |
| 2011/0071445 A1* | 3/2011 | Imboden | A61H 23/0263 601/46 |
| 2011/0098781 A1* | 4/2011 | Mantle | A61H 1/008 607/46 |
| 2011/0230938 A1* | 9/2011 | Simon | A61N 1/36014 607/63 |
| 2013/0046212 A1* | 2/2013 | Nichols | A61H 7/005 601/18 |

* cited by examiner

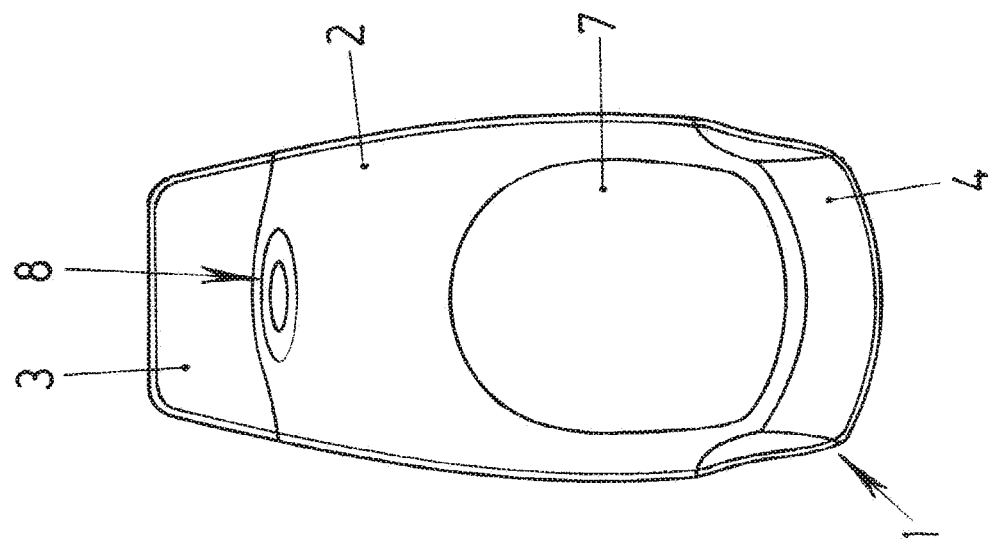
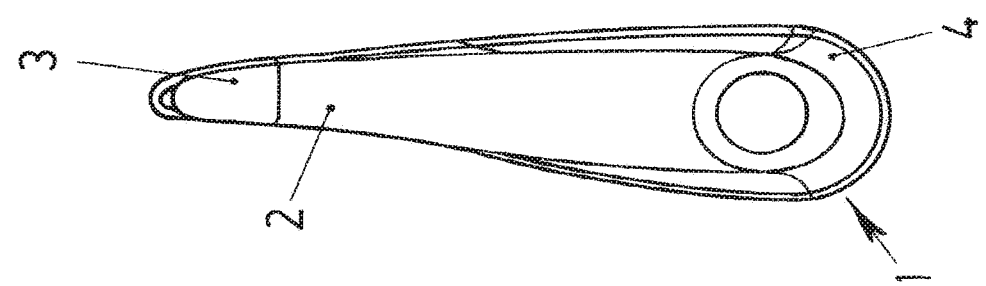
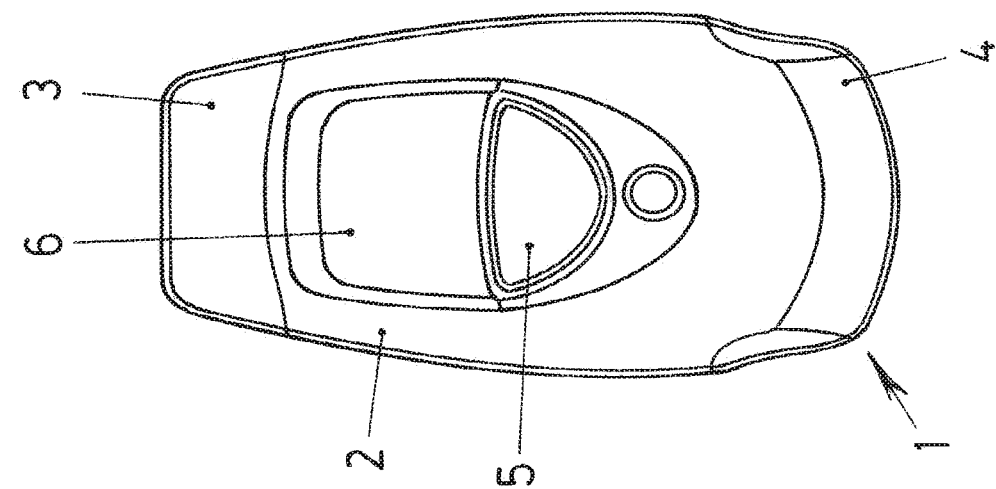

HAND-HELD DEVICE FOR ELECTRICALLY POWERED SKIN TREATMENT

CROSS REFERENCE TO RELATED APPLICATIONS

This application is a divisional of U.S. application Ser. No. 14/372,433, filed Jul. 15, 2014 which was the National Stage of International Application No. PCT/EP2013/000112, filed Jan. 16, 2013, which claims priority to German Patent Application No. 10 2012 009 514.7, filed May 14, 2012, and German Patent Application No. 10 2012 000 563.6, filed Jan. 16, 2012, the entire disclosures of which are expressly incorporated by reference herein.

BACKGROUND AND SUMMARY OF THE INVENTION

The invention relates to a hand-held device for electrically powered skin treatment, comprising:
a first outer electrode, which is in contact with the hand when the device is held in the user's hand for use, a second outer electrode, which can be placed on the area of skin to be treated, and an electrical energy source, the poles of which are electrically connected to the electrodes during operation of the device.

A device of this type is described in WO 2005/087308 A1. To use the device, the user picks it up and places a cap functioning as an electrode on the areas of skin to be treated. An electrically conductive contact to the hand is produced by the first electrode, and an electrically conductive contact to the area of skin to be treated is produced by the second electrode. Since the two electrodes are each connected to a pole of an electrical energy source, an electric circuit is produced which includes the user's body, whereby a positive or a negative electric current flows from the cap into the area of skin to be treated, depending on polarity.

This can be used to increase the efficacy of treatment creams and cleansing creams, since the active ingredients of a treatment cream are transported into the skin by means of the electric current and, with opposite polarity, dirt is transported from the skin into a cleansing cream.

The device is further provided with a multiplicity of exchangeable caps, the design of these caps being adapted to the skin surface to be treated. There is a first cap having a relatively smooth surface, a second cap, which is formed in a comb-like manner and which can be used, above all, to treat the scalp, and a third cap having an undulating structure, which is associated with a massaging effect. Good results have been achieved with the device, both in the case of skin cleansing and in the case of introduction of active ingredients. However, this is to be improved further.

The invention is therefore based on the object of further improving the efficacy of the device.

To achieve the object, it is proposed to fix an electrically operated vibrator in or on the device.

Such a vibrator vibrates the device so that, during operation, the device produces an intensified massaging effect, whereby the skin pores are widened and the dirt is better passed from the skin, or the active ingredients are better passed into the skin.

The massaging effect is particularly pronounced if the vibrator is fixed in the vicinity of the second outer electrode because the part of the device located on the area of skin to be treated then vibrates particularly intensely.

The invention is preferably used in a device which comprises:

a base, which is designed to be grasped by a hand, the first outer electrode being provided on the base,
a cap to be placed detachably on the base, said cap comprising the second outer electrode which can be placed on the area of skin to be treated,
the electrical energy source being arranged in the base.

In such a device, the electrically operated vibrator is fixed in or on the cap, and therefore in the direct vicinity of the second electrode.

Preferably, contact means on the cap and on the base, which serve to establish an electrical connection between the second electrode and the electrical energy source, are designed and arranged in such a manner that they are brought into contact when the cap is placed on the base, whereby the vibrator is in switchable electrically conducting contact with the electrical energy source in the base.

The energy source may be batteries or accumulators, which are inserted into a compartment in the base. Insofar as accumulators are to be provided for the device, it is conceivable to also provide the device with a charging apparatus with which the accumulators in the device can be charged.

Since the energy source is arranged in the base, but the vibrator and one electrode are arranged in or on the cap, it is necessary to produce an electrical connection. The invention provides a first and a second electrical contact between the base and the cap, both electrical contacts comprising a base contact element and a cap contact element, the base contact element being arranged in the base and the cap contact element being arranged in the cap in such a way that the contacts are closed when the cap is placed on the base, the electrical connection between the energy source and the second electrode being produced by the first contact, and the electric circuit, which supplies power to the vibrator, running through the first and second contacts.

Since the first contact is used both to supply power to the second electrode and to connect the vibrator, merely two contacts are required, although three connections (one for the electrode, two for the drive of the vibrator) are produced in total.

The contact elements preferably comprise pins, the end faces of which contact one another when the cap is attached, one of the contact elements of each contact being spring-mounted in axial direction. The cap is held on the base by means of a releasable catch.

When the cap is placed on the base, the end faces of the pins press against one another so that an electrical contact is produced. At the same time, a resilient force is exerted onto the cap as a result of the bias of the springs, and therefore the cap is pressed resiliently away from the base and detaches easily from the base as soon as the catch, which holds the cap on the base, is released.

Since the second contact merely supplies power to the vibrator, the contact element is to be inserted in the cap so as to be insulated with respect to the second electrode. This is then particularly necessary if the cap consists entirely of an electrically conductive material, or if an outer layer of the cap consists of an electrically conductive material, the cap contact element of the first electrical contact being connected to the material in an electrically conductive manner, and the cap contact element of the second electrical contact being electrically insulated with respect to the conductive material.

To implement the second electrode, it is provided that the cap consists entirely of an electrically conductive material or an outer layer of the cap consists of an electrically conductive material, that the cap contact element of the first electrical contact is connected to the material in an electrically conductive manner, and that the cap contact element of the second electrical contact is electrically insulated with respect to the conductive material.

Since—as explained above—the device allows the polarity of the electrodes to be exchanged, this means that the polarity of the power supply of the vibrator is also reversed. The vibrator must therefore have an electric drive which is not sensitive to a swapping of polarity. In the simplest case, the vibrator is an electric motor, a cam being fastened to the shaft of said electric motor. However, vibration exciters in which a mass is drawn first in one direction and then in the other direction in quick succession by electromagnets are also conceivable.

The electric motor, onto the shaft of which a cam is fixed, can be arranged in various alignments in the cap. On its lower end, the cap has a plug-on region, which can be plugged onto the base, and on its upper end, it forms the second outer electrode. In order to oscillate the electrode back and forth on the skin so that a particular cream can be rubbed in, it is provided that the axle and the shaft of the electric motor extend essentially parallel to a virtual line between the plug-on region and the second outer electrode.

According to an alternative embodiment, the axle and the shaft of the electric motor extend essentially transverse to a virtual line between the plug-on region and the second outer electrode. Due to this arrangement, an alternating pressure is induced on the skin so that the respective cream is pressed into the skin.

If at all possible, integration of the vibrator in the cap should take place in a manner in which design elements of the hitherto known device can be retained as far as possible without any changes. The invention thus provides that in the cap a bottom is inserted which on its upper side facing the cap comprises a retainer for the vibrator.

According to the invention, the pins of the cap are arranged in the bottom of the cap, whereby the two pins that form the cap contact elements penetrate the bottom. In this arrangement, the pins project both towards the upper side and towards the underside of the bottom, whereby one of the pins is in electrically conductive contact with the second electrode.

Furthermore, the invention provides that a circumferential rubber seal is arranged on the bottom, the rubber seal sealing the bottom from the interior wall of the cap so that the chamber in the peak of the cap, in which the vibrator is accommodated, is protected from water and the entry of humidity.

Furthermore, it is provided that two tabs project from the underside of the bottom, with one of these tabs comprising a slot. That is to say that the cap with the vibrator is to be compatible with basic devices that are already on the market. These comprise a catch that engages a slot in the interior wall of the cap in order to hold the cap to the base. Since the cap with the vibrator is elongated and in its lower region is significantly enlarged, the tabs are required in order to fix the cap to the plug-on region of the basic device, whereby the slot acts as a counterpart to the catch on the base.

To ensure that contact with the second electrode is established, in the cap a connector socket is formed, the inside of which is in electrically conductive contact with the second electrode, whereby the connector socket is aligned in such a manner that one pin is inserted in the connector socket when the bottom is inserted in the cap.

The bottom with the two pins thus only needs to be pushed into the cap. In this process one of the pins is inserted into the connector socket and establishes a conductive connection with the second electrode. The pin ends projecting towards the underside of the bottom establish contact with two base pins on the base and, by means of the base pins, a switchable connection to the energy source in the base is established.

In order to achieve the supply of current to the electrical drive of the vibrator, the upper ends of the pins have soldering lugs to which the power supply cables to the electric motor are soldered. The invention thus provides that the soldering lugs that project on the upper side of the bottom are attached to the ends of the pins.

In order to fix the bottom even better in the cap and in order to even better transmit the vibrations of the bottom, caused by the vibrator, to the cap or to the region of the cap that forms the electrode, it is provided that the bottom is penetrated by two retaining pins that project towards the upper side. In the caps there are retaining bushes into which the retaining pins are inserted or screwed when the bottom is inserted in the cap.

Preferably, pillars that emanate from the peak of the cap are arranged in the cap, whereby the retaining bushes are formed in the pillars and their openings lead to the end faces of the pillars.

It would also be imaginable for transverse webs to be arranged in the cap, these transverse webs interconnecting opposite sections of the cap, and for the retaining bushes to be formed in the transverse webs.

The cap encloses a space in the peak of the cap, where the vibrator is accommodated, whereby the vibrations of the vibrator are transmitted to the cap by way of the retainer and the bottom.

In order to keep the design of the device simple, a switching device, which can be adjusted by the user of the device, is provided in the base and produces the electrical connections between the energy source and the electrodes, and the vibrator is also connected to the electrical energy source by the switching device. There is thus a common energy source for the electrodes and the vibrator.

The switching device is preferably provided with an electronic memory, in which the parameters of operating states to be selected are stored and can be selected by the user by means of a button, one of the parameters relating to the polarity of the electrodes and the vibrator being of the kind that operates independently of the polarity of the applied voltage.

For the vibration effect to be as great as possible, the invention further provides that the cap has two laterally protruding tongues on its end distanced from the base, the upper faces of said tongues forming a continuous surface which can be brought into contact with the skin to be treated, the vibrator being in direct mechanical contact with at least one of the tongues. The upper face of the continuous surface is preferably provided with a fluting so that the effect on the skin is intensified.

The caps provided for operation of the device do not all have to be provided with a vibrator. In some applications, it is sufficient to carry out an electrotherapy treatment on its own.

To keep the interval between charging of the batteries as long as possible, it must be ensured that the power consumption of the device is minimized to the greatest extent possible. This is the case in particular if the device has a vibrator that causes the second electrode, which is placed on the skin area to be treated, to shake. In order to minimize the power consumption of such a device, the invention provides a device for detecting a current flow through the second electrode, a switch in the connection of the drive of the vibrator to the batteries, and a control device that is designed so that the switch is only closed when a current flows through the second electrode.

In other words, the vibrator is switched on only if the second electrode is placed onto the skin area to be treated and via the second electrode a current flows through the skin. This current flow is detected and used by a control device in order to activate the switch. The device can be implemented electronically. This means that the switch is designed as a transistor.

Furthermore, it is provided for the device to comprise rechargeable batteries whose poles during operation of the device are in electrical connection with the electrodes. The batteries are accommodated in a compartment that is covered by a shell-like housing cover whose outside forms a section of the exterior area of the device housing. Furthermore, a charging circuit is provided. The compartment is covered by a removable compartment cover whose inner side is directed to the batteries in the compartment and on whose outer side a connector socket with at least two poles is arranged that is connected to the charging circuit. The compartment cover is arranged within the housing cover.

The connector socket is preferably a connector socket according to the USB standard.

In the following, the invention is explained in more detail with reference to exemplary embodiments.

BRIEF DESCRIPTION OF THE DRAWINGS

FIG. 1 a, b, c show views of a device according to the invention, whereby a rounded structure is provided as a cap, FIG. 2 a, b, c show different cap designs for use with the device according to the invention.

DETAILED DESCRIPTION OF THE DRAWINGS

Figure 2A:
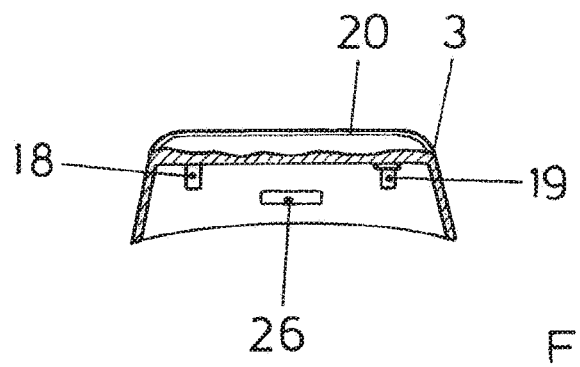

Reference is first made to FIG. 1. As shown in the three views in FIG. 1, the device 1 according to the invention is approximately as large as the palm of a hand and has a flat, rectangular design. It comprises a base 2 and a cap 3 fitted thereon. A compartment 4 for accommodating batteries, which in this exemplary embodiment serve as the energy source to operate the device 1, is located at the lower, short end of the base 2.

The exchangeable cap 3 is fitted on the opposite, upper short end of the base 2, this end being narrower than the lower end. A button 5 for selecting a treatment program is arranged on the front side of the base 2, the selected treatment program being shown on a display 6 positioned there above. A first electrode 7 having a large surface area is located on the rear side and, above this, a press key 8 for actuating a catch, by means of which the cap 3 is held on the base 2.

Different cap designs are illustrated in FIG. 2 in longitudinal section. FIG. 2a shows the cap 3 already illustrated in FIG. 1, this cap having a rounded upper edge.

Figure 2B:
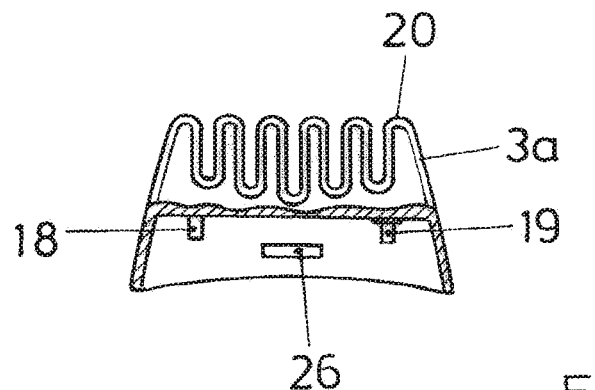
Figure 2C:
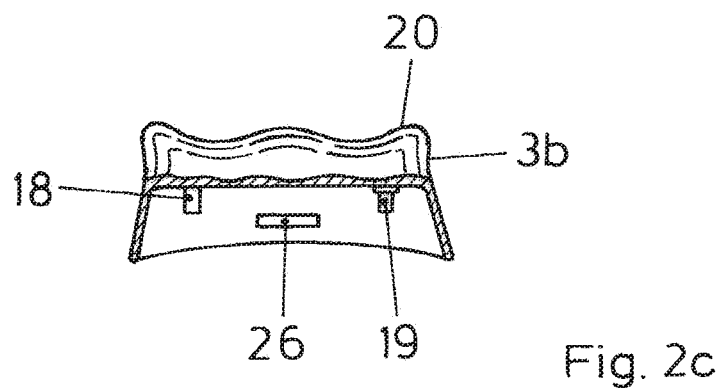

The cap 3a according to FIG. 2b has a comb-like structure and is therefore particularly suitable for treating the scalp. FIG. 2c shows a cap 3b having an undulating edge, whereby it is possible to intensify the pressure on the skin at certain points so that a massaging effect is produced on the skin when the cap 3b is moved back and forth.

Figure 3:
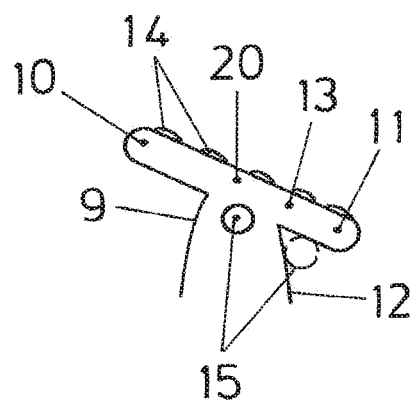
FIG. 3 shows the cross-section of a cap design which is particularly suitable for operation with a vibrator.

A further cap 9 is illustrated in cross-section in accordance with FIG. 3 and illustrates a modification of the cap 3 according to FIG. 2a. Two tongues 10, 11 are formed on the upper edge of the cap 9 and together form a platform 13 which is inclined to the base 12 of the cap 9. The upper face of the platform 13 forms a continuous surface which can be placed on the skin and is provided with ribs 14.

This design is particularly suitable for connection to a vibrator 15. This is either fixed preferably in the acute angle between one tongue 11 and the base 12 of the cap 9 (dot-dash line), or in the head of the base 12 of the cap 9 (solid line). Placement in one of the tongues 10, 11 is also conceivable.

Figure 4:
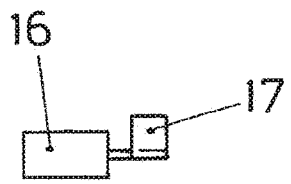
FIG. 4 shows a motor having a cam, FIG. 5 a, b show an arrangement of contact elements for producing an electrical contact between the base and the cap.

In the simplest case, according to FIG. 4, the vibrator 15 comprises an electric motor 16, a cam 17 being fixed to the shaft of said electric motor. The shaft can be oriented in relation to the device in any manner. An orientation parallel to the upper edge of the cap 9 is possible, for example.

Figure 9:
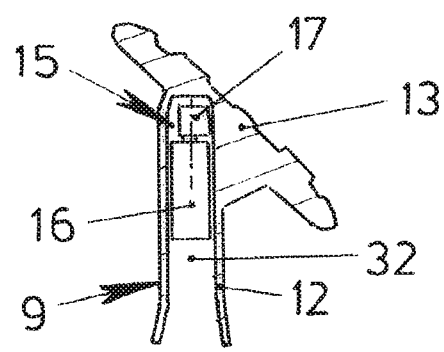
FIG. 9 shows an alternative arrangement of the vibrator.

In FIG. 9, a further possible arrangement of the electric motor 16 of the vibrator 15 is shown. The base 12 of the cap 9 comprises a cylindrical recess 32, the axis of which extends in the direction of the platform 13. In this embodiment, the electric motor 16 is arranged coaxial to the axis of the recess 32, whereby the shaft of the electric motor protrudes with the cam 17 into the platform 13. According to this embodiment, the shaft is arranged with the cam 17 vertical to the upper edge of the cap 9 and therefore extends between the lower area of the cap 9, which is plugged onto the base 2, and the upper area of the cap 9, which forms a second outer electrode 20.

As can be seen from FIG. 2a to FIG. 2c, two metal pins 18, 19 are located inside the cap 3, 3a, 3b, whereby one of the pins 18 is electrically connected to the cap 3, and the other pin 19 is insulated with respect to the cap 3, 3a, 3b. The caps 3, 3a, 3b consist of a conductive material or have at least a coating made of a conductive material, this material forming the second electrode 20. The first pin 18 is thus connected to this material, whereas the second pin 19 is insulated with respect thereto.

The cap 9 according to FIG. 3 is similarly provided with pins, although this is not shown.

As can be seen from FIG. 5, two spring-mounted metal counter-pins 21, 22 are fixed on the upper edge of the base 2 and are oriented in line with the pins 18, 19 in the base 2. The counter-pins 21, 22 are each pressed against a stop by a spring 23, 24 arranged in a shoulder 25, so that they protrude slightly beyond the upper edge of the shoulder 25. If the cap 3a, 3b, 3c, 9 is fitted onto the shoulder 25 of the base 2, two closed electrical contacts are thus produced.

Figure 6:
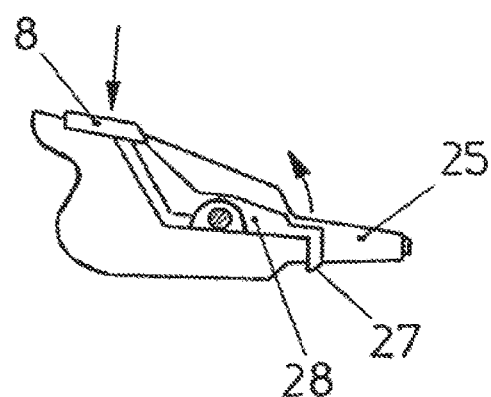
FIG. 6 shows an embodiment of a latching catch.

As illustrated in FIG. 2, a slot 26 for a catch is located in each of the caps 3a, 3b, 3c. The cap 9 of FIG. 3 is formed accordingly. As shown in FIG. 6, such a catch 27 is located on the end of a lever 28, which is mounted rotatably on the base 2 and of which the outer end is connected to the press key 8 so that the catch 27 is pushed out of the slot 26 when the press key 8 is actuated.

Figure 5A:
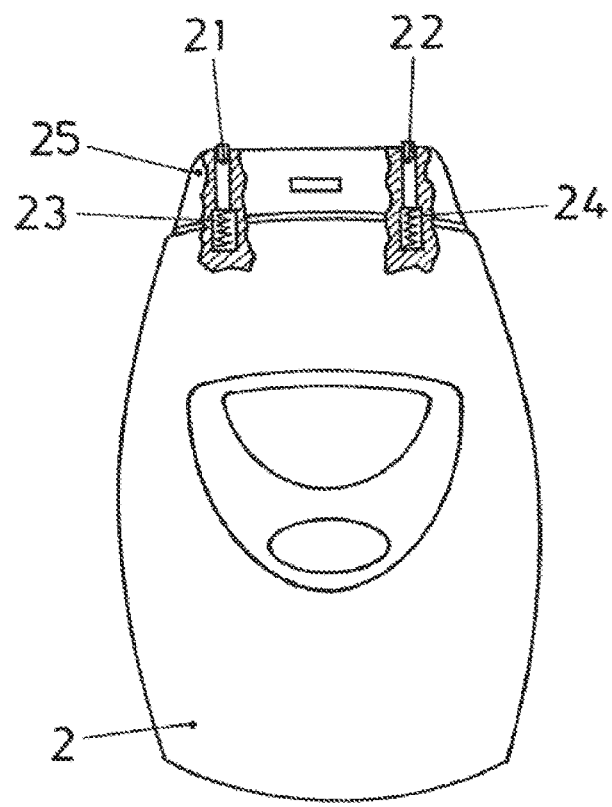
Figure 5B:
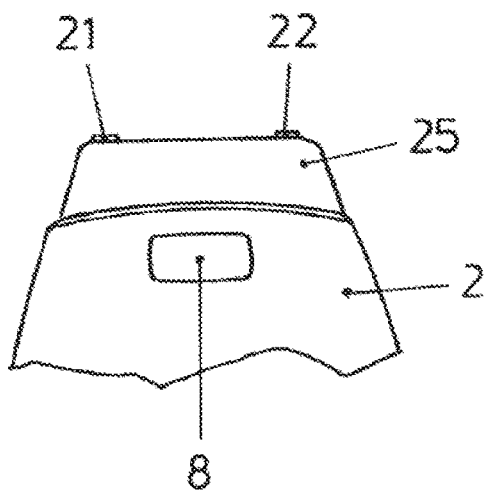

As can be seen from FIG. 5a and FIG. 5b, the counter-pins 21, 22 are spring-mounted on the base so that they exert a pressure onto the pins 18, 19 in the cap 3, 9. If the press key 8 is actuated, the counter-pins 21, 22 press the cap 3, 3a, 3b, 9 slightly away from the base 2 so that the cap can be easily removed.

Figure 7:
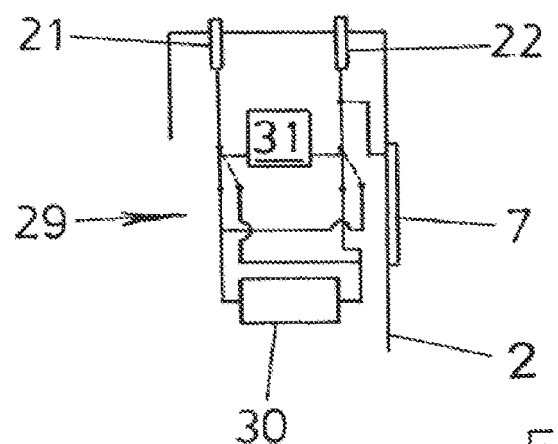
FIG. 7 shows an electrical circuit for operating the device.

A circuit diagram is illustrated schematically in FIG. 7. The drive of the vibrator, that is to say the electric motor 16 in the exemplary embodiment, is connected between the two pins 18, 19 in the cap 3, 9, whereas the first pin 18 is merely connected to the second electrode 20 on the cap 3, 9.

The two counter-pins 21, 22, which are connected to a power source 30 (batteries) by a switching device in the form of a changeover switch 29, are located on the base 2. The counter-pin 21, which contacts the insulated pin 18 in the cap 3, 9, has a connection to the first electrode 7 on the base 2.

If the cap 3, 9 is then fitted onto the base 2—as indicated in FIG. 7—(a coding prevents the contacts from being swapped), a first electric circuit comprising the power source 30 and the electric motor 16 is produced and runs through the two pairs of pins, and a second electric circuit, which runs through the first contact of the second electrode 20, to the first electrode 7 via the user's body, and back to the power source 30, is produced during operation.

The changeover switch is provided in the form of a transistor circuit which is controlled by a control device 31. The control device 31 contains an electronic memory in which a plurality of operating modes are stored. The operating modes are determined by the following parameters: duration of the treatment, polarity of the electrodes, and connection of the vibrator. The user can select a specific operating mode by actuating the button 5, this operating mode being shown on the display 6.

A skin treatment generally comprises a first step in which a cleansing cream is first applied and the device is operated with a first polarity, whereby dirt passes from the skin into the cleansing cream by the flow of current. Caps 3 which do not contain a vibrator are used in this case because the creams are not to be worked into the skin.

In a second step, once the cleansing cream has been removed, a treatment cream is applied and the device 1 is operated with a second polarity so that the active ingredients from the treatment cream can penetrate into the skin. With this approach, caps 9 are used which do comprise a vibrator 19 so that, in addition to the effect of the current which transports the active ingredients into the skin, a massaging-in effect is also provided, by means of which the active ingredient is rubbed into the skin. In addition to the increased efficacy, a pleasant feeling during the treatment process is also produced since the user finds a vibrating massage pleasurable.

Figure 8:
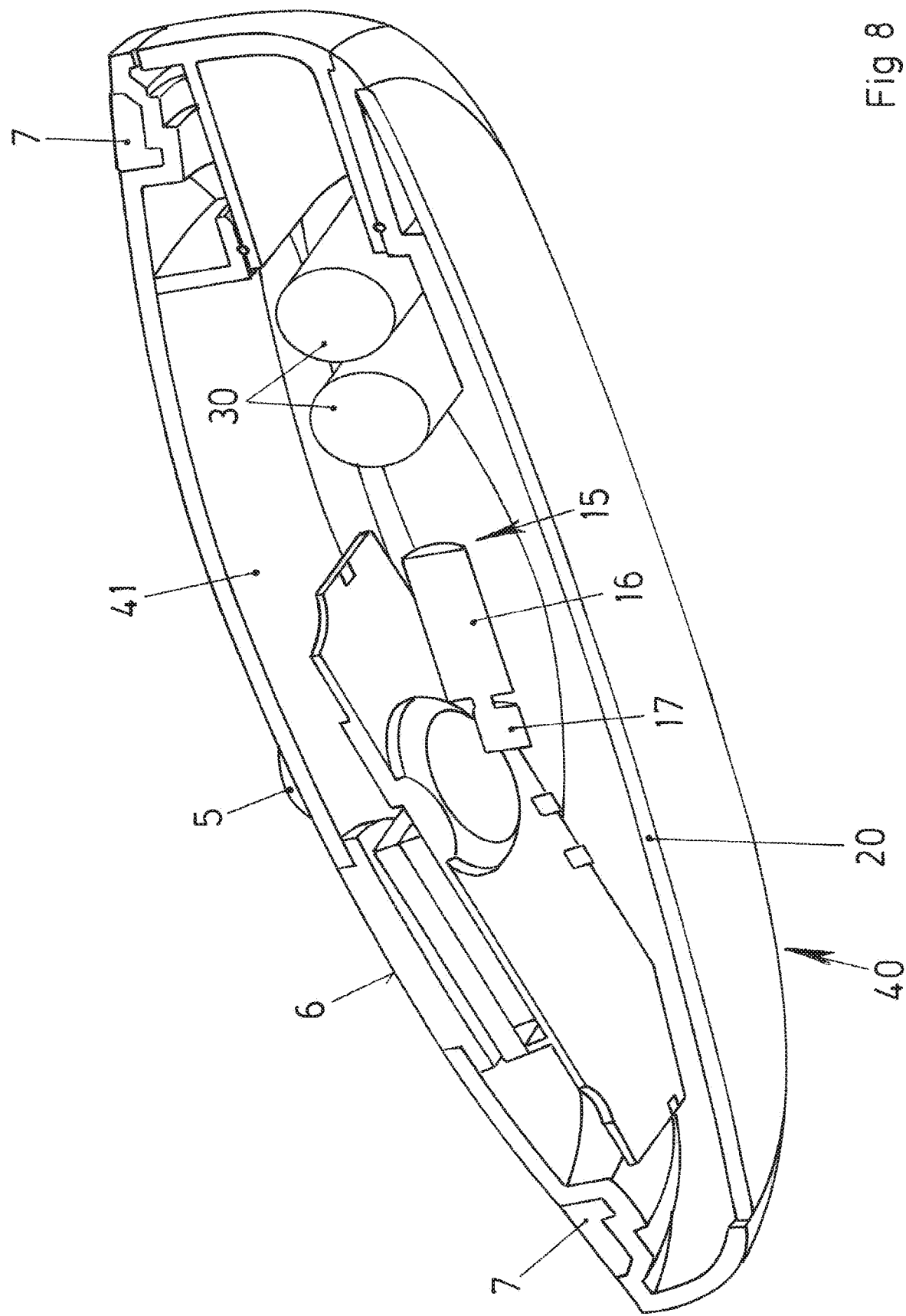
FIG. 8 shows a further embodiment of the device according to the invention.

FIG. 8 shows a device 40 in cross-section, said device being suitable in particular for cellulite treatment of large skin surfaces.

A second electrode 20, which takes up almost the entire underside, is located on the underside of a shallow housing 41 and is placed on the area of skin to be treated. A display 6 and a button 5 for selecting a treatment program are located on the upper side.

A first electrode 7, which is in contact with the hand holding the device 40, is located peripherally on the outer edge of the upper side of the housing 41. A power source 30 in the form of batteries, and a vibrator 15, which comprises an electric motor 16 having a cam 17, are located inside the housing 41. The vibrator 15 is fixed centrally above the second electrode 20 by means of a socket (not illustrated) on the lower wall of the housing 41, and thus vibrates the wall together with the second electrode 20 when operated.

The circuitry of the electrodes 7, 20 of the electric motor 16 and of the power source 30 corresponds to that shown in FIG. 7, however the pins 18, 19; 21, 22 are replaced by continuous connections. The pins are not necessary since the device 40 does not have any exchangeable caps 3, 9 with second electrodes 20 in this embodiment.

Figure 10:
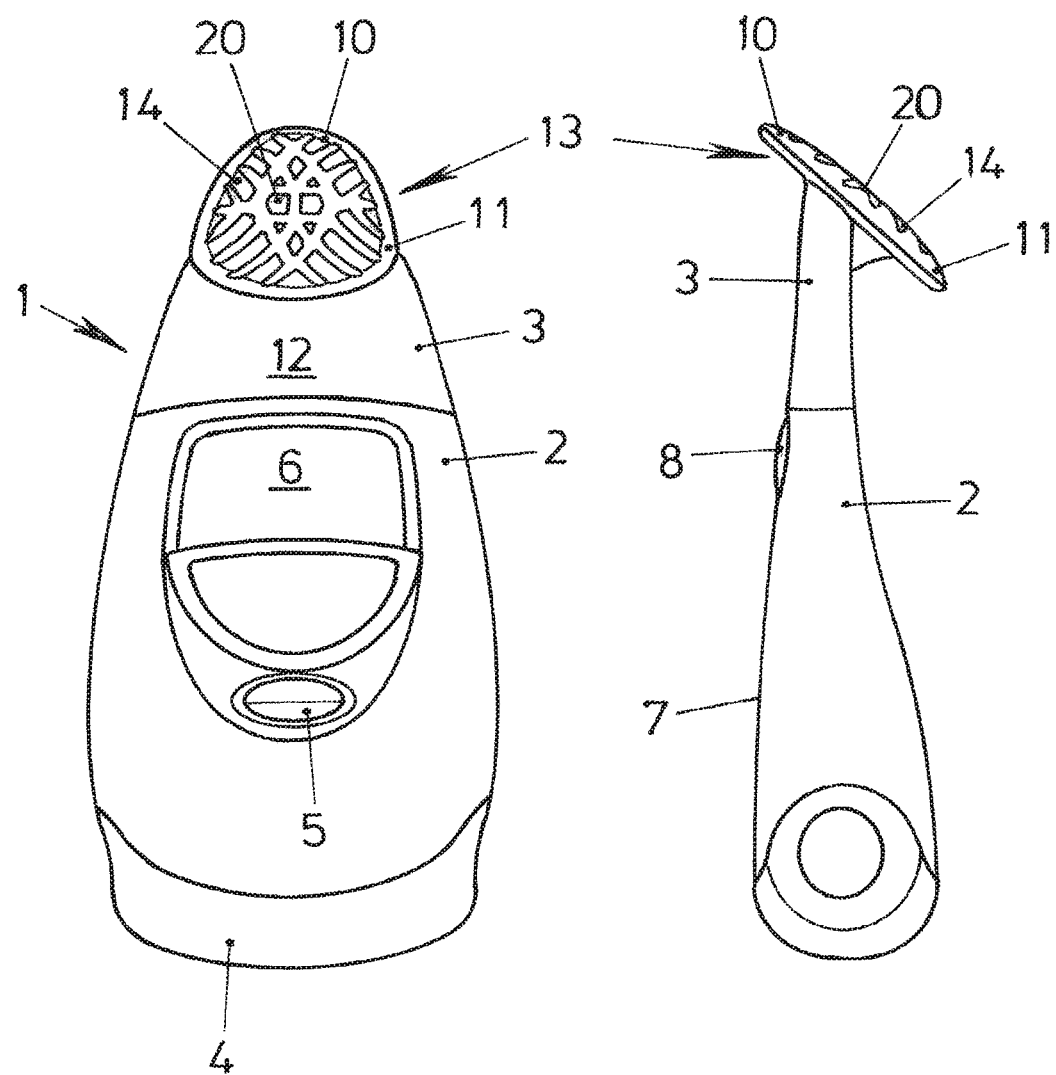
FIG. 10 shows two exterior views (a front view and a lateral view) of a device for skin treatment according to the invention, with said device comprising a hand-held base and a cap with a platform, which forms an electrode, for placement onto the skin.

Now, reference is made to FIG. 10. As shown in the two views, the device 1 according to the invention is approximately as large as the palm of a hand and has a flat, rectangular design. It comprises a base 2 and a cap 3 fitted thereon. A compartment 4 for accommodating batteries, which in this exemplary embodiment serve as the energy source to operate the device 1, is located at the lower, short end of the base 2.

The exchangeable cap 3 is fitted on the opposite, upper short end of the base 2, this end being narrower than the lower end. A button 5 for selecting a treatment program is arranged on the front side of the base 2, the selected treatment program being shown on a display 6 positioned there above. A first electrode 7 having a large surface area is located on the rear side and, above this, a press key 8 for actuating a catch, by means of which the cap 3 is held on the base 2.

Two tongues 10, 11 are formed on the upper edge of the cap 3 and together form a platform 13 which is inclined to the base 12 of the cap 3. The upper face of the platform 13 forms a continuous surface which can be placed on the skin and is provided with ribs 14.

In the simplest case, according to FIG. 11, FIG. 3, FIG. 4, and FIG. 5, the vibrator 15 comprises an electric motor 16, a cam 17 being arranged on the shaft of said electric motor 16.

Within the base 12 of the cap 3 there is a cylindrical recess 32, the axis of which extends in the direction of the platform 13. In this embodiment, the electric motor 16 is arranged coaxial to the axis of the recess 32, whereby the shaft of the electric motor protrudes with the cam 17 into the platform 13. According to this embodiment, the shaft is arranged with the cam 17 vertical to the upper edge of the cap 3 and therefore extends between the lower area of the cap 3, which is plugged onto the base 2, and the upper area of the cap 3, which forms the second outer electrode 20.

As is further shown in FIG. 11, FIG. 12, FIG. 13, FIG. 14, two metal pins 18, 19 are located inside the cap 3, whereby one pin 18 is electrically connected to the cap 3 and the other pin 19 is insulated from the cap 3. The cap 3 with the platform 13 consists of a conductive material or has at least a coating made of a conductive material so that the platform 13 forms the second electrode 20.

Figure 11:
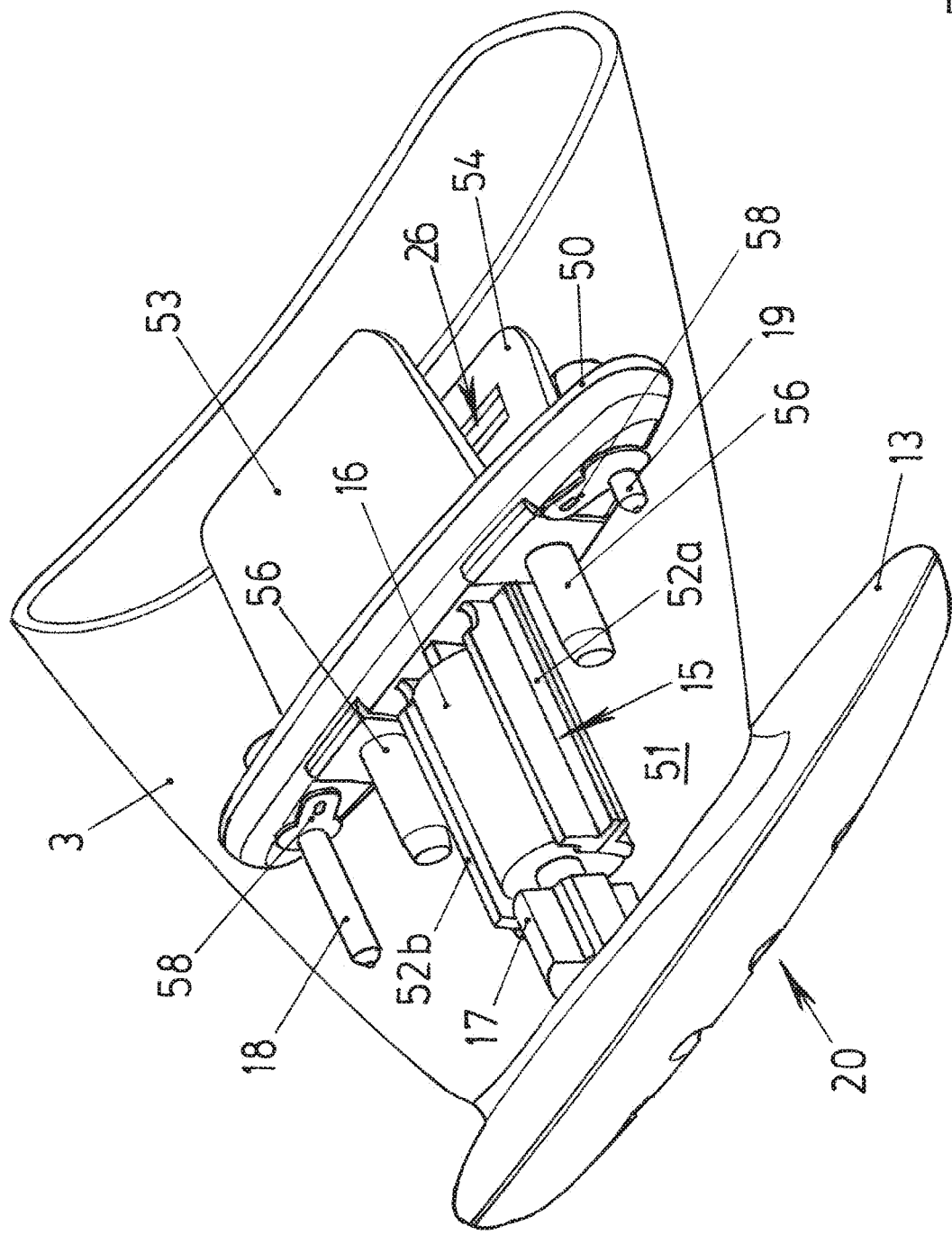
FIG. 11 shows a perspective and transparent view of the cap, with a bottom and a vibrator held to the bottom being shown in the interior of the cap.

FIG. 11 shows a perspective view of the cap 3 which in the illustration is transparent so that a bottom 50 that is inserted in the cap may be seen. The bottom 50 is located approximately at half the height in the cap 3, whereby its circumferential contour corresponds to the cross-section of the cap 3 at this position, and consequently the bottom 50 encloses a chamber 51 in the peak of the cap underneath the platform 13. At the upper side of the bottom 50, the upper side facing the platform 13, there are two arms 52a, 52b that project perpendicularly from the bottom 50, these arms 52a, 52b forming the recess 32 for the electric motor 16. Between the arms 52a, 52b the electric motor 16 is located, with its shaft with the cam 17 being aligned in the direction of the platform. On the underside of the bottom 50 there are two tabs 53 and 54 that are aligned so as to be parallel to each other and that encompass on both sides a plug-on region (not shown in the drawing) on the base. One tab 54 comprises a slot 26 which is engaged by a catch (also not shown in the drawing) on the base in order to hold the cap 3 to the base.

Figure 12:
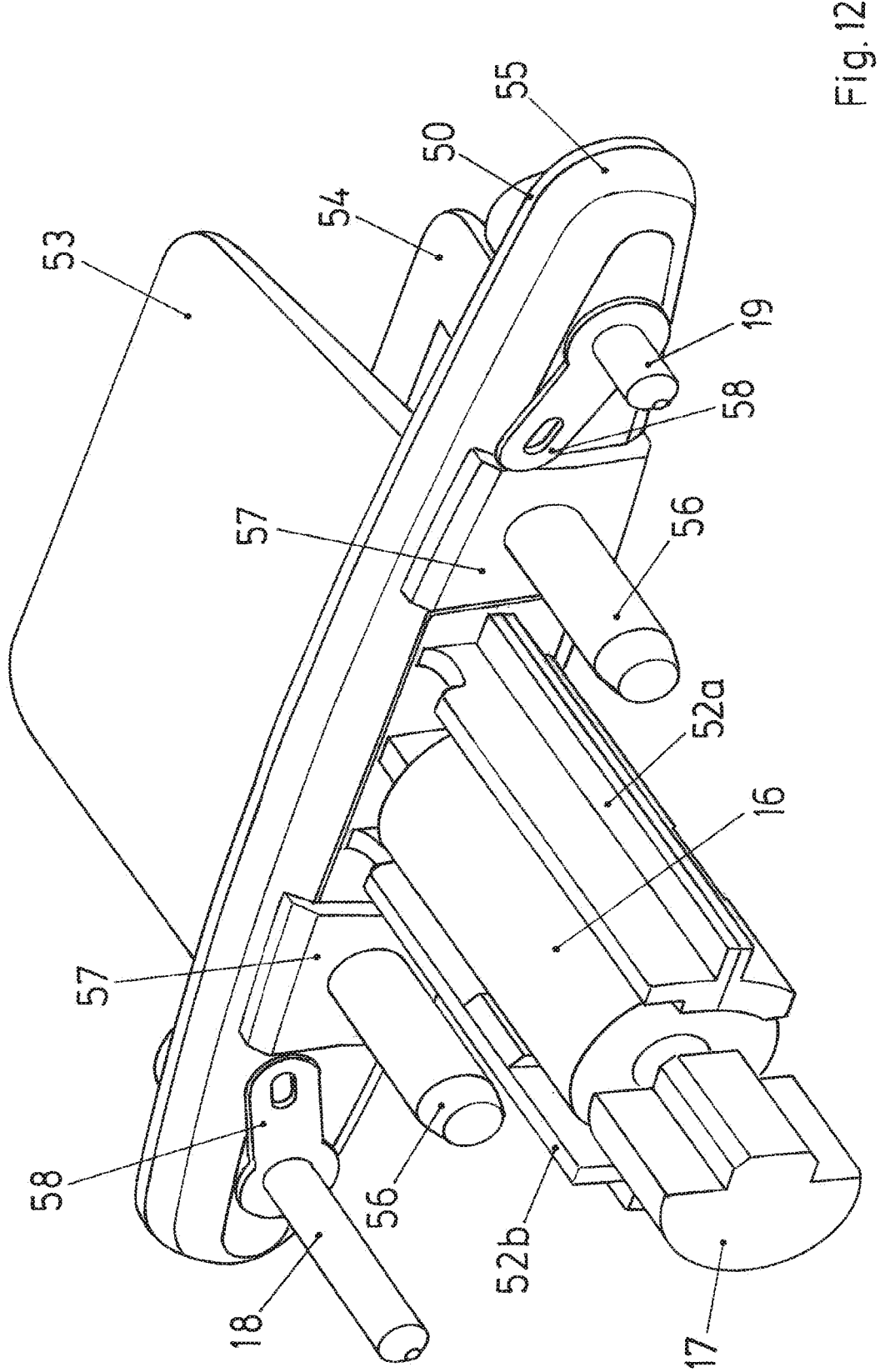
FIG. 12 shows a perspective view of the cap with the vibrator.

FIG. 12 shows an enlarged view of the bottom 50. Said bottom 50 comprises a circumferential rubber seal 55 that conforms to the interior wall of the cap 3. The two arms 52a and 52b are in the middle part of the bottom 50; at their facing sides they are designed so as to be at least in part cylindrically curved, whereby the envelope of the curvatures forms a cylinder that accommodates the cylindrical electric motor 16.

To the left-hand side and the right-hand side of the two arms 52a, 52b there is a retaining pin 56, each retaining pin 56 projecting perpendicularly from the bottom 50 and each being enclosed by a sealing sheet 57. The two sealing sheets 57 form an entity with the rubber seal 55.

Further to the outside of the bottom 50, the first pin 18 and the second pin 19 are arranged, whereby the first pin 18 is designed so as to be longer than the second pin 19. A soldering lug 58 is placed on each of the pins 18 and 19.

Figure 13:
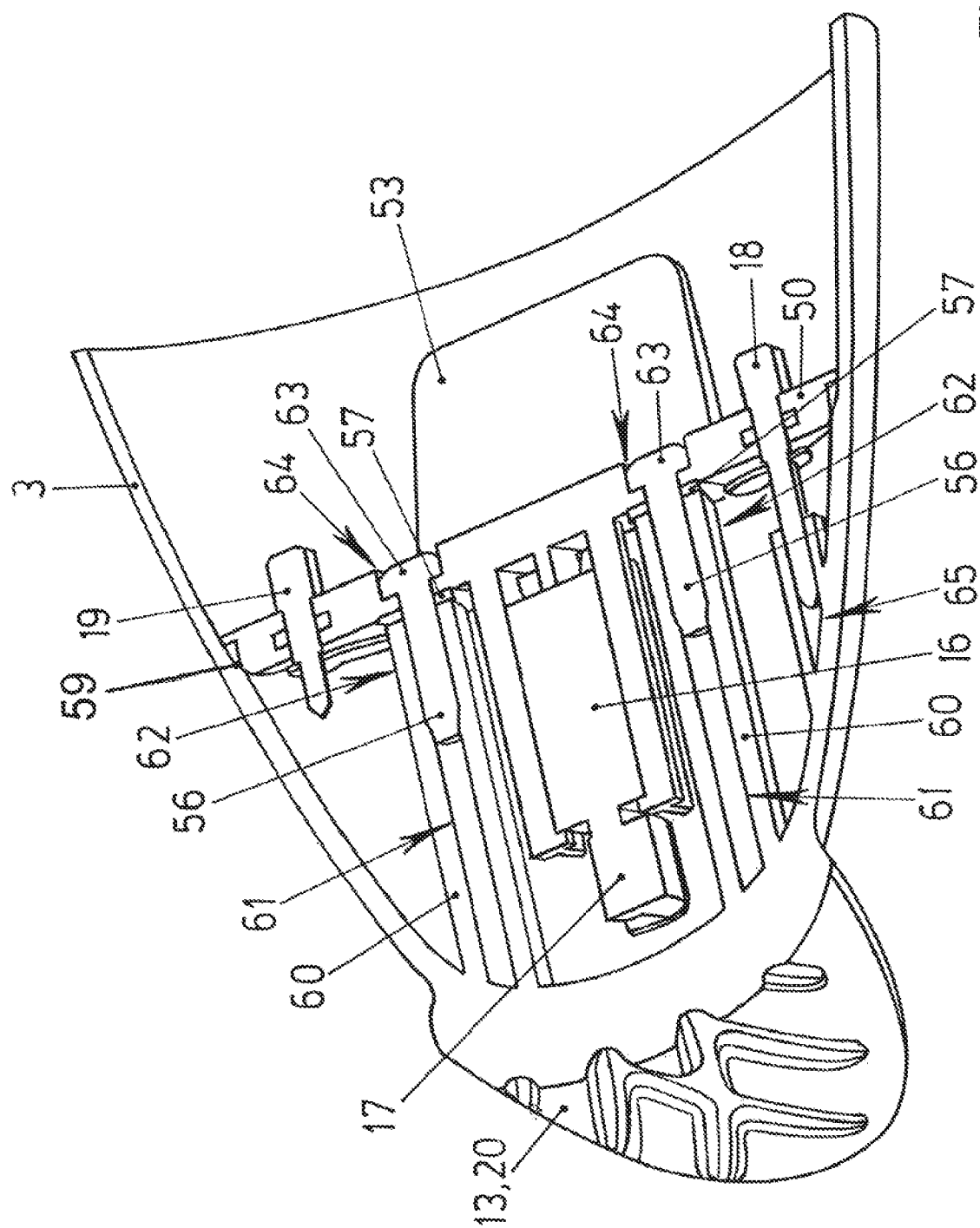
FIG. 13 shows a longitudinal section of the cap with the vibrator.

The cross-sectional view of FIG. 13 clearly shows the connection of the bottom 50 to the cap 3. The base 12 of the cap comprises a conically expanding shape so that the bottom 50 can be slid from below into the cap 3 until it abuts against a step 59. From the peak of the cap 3 two pillars 60 emanate, each pillar 60 comprising a cylindrical channel 61. The retaining pins 56 are plugged or screwed into these channels 61, whereby the faces of the pillars 60 rest against the sealing sheets 57 so as to provide a seal. The retaining pins 56 comprise heads 63 that are located in indentations 64 on the underside of the bottom 50. The retaining pins 56 are thus held by clamping force in the channels 61 or are screwed into the channels 61 which form retaining bushes 62 for the retaining pins 56 so that the bottom 50 is fixed in the cap 3.

However, it is not the sole task of the retaining pins 56 to hold the bottom 50 in the cap 3; they also establish a vibration-transmitting connection to the peak of the cap 3 where the platform 13 is located. The vibrations caused by the rotating cam 17 are thus directly transmitted to the platform 13.

The pins 18, 19 are located in through-holes in the bottom 50, whereby the lower ends project to the underside of the bottom 50 where they establish contact with counter-pins (not shown in the drawing) on the base.

As already mentioned, the ends of the pins 18, 19 comprise soldering lugs 58. The end of the second pin 19 finishes freely in the chamber 51, while the first pin 18 enters a connector socket 65 on the inside of the cap 3, thus establishing electrically conductive contact with the cap 3. This is again ensured in that the cap 3 itself is made of metal or comprises a plastic material with a metal coating that extends into the connector socket 65.

The illustrated cap 3 for a device for skin treatment thus comprises the base 2 and the cap 3, into which a vibrator 15 is inserted that is attached to the bottom 50. The bottom 50 is plugged into the cap 3 where it is held by retaining pins 56. Pins 18, 19 on the one hand establish an electrical connection to the second electrode 20 on the cap 3, and on the other hand the supply of power to the electric motor 16 of the vibrator. The two tabs 53, 54 ensure that known bases can continue to be fixed onto the cap and are compatible with the cap.

Figure 14:
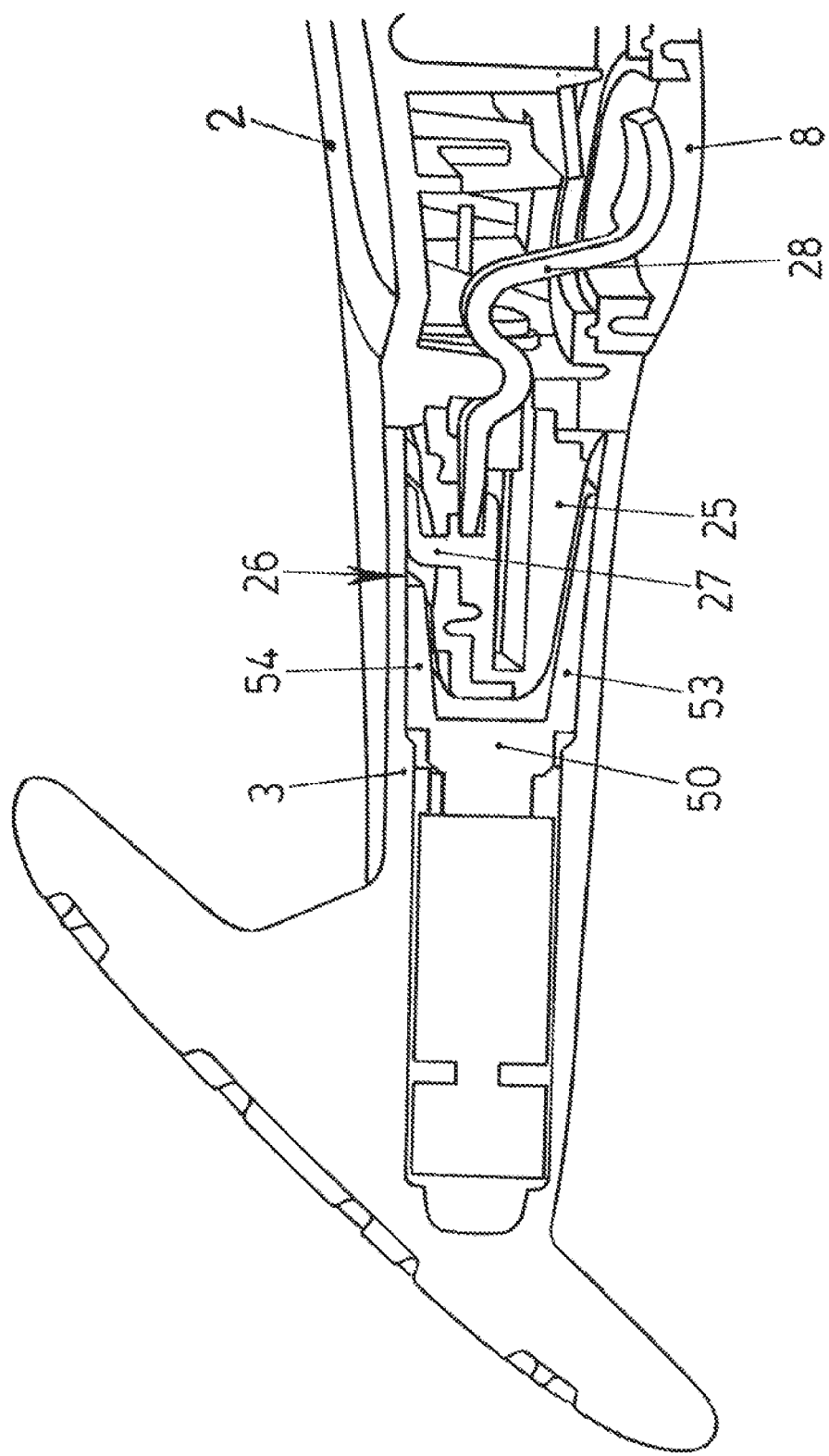
FIG. 14 shows a longitudinal section (perpendicular to the longitudinal section of FIG. 13) of the cap with the vibrator and the upper part of the base.

FIG. 14 shows a longitudinal section of a cap 3 placed on a base 2. A receiving region of the base 2, this receiving region being formed by a shoulder 25, extends between the two tabs 53 and 54, as a result of which the two tabs 53, 54 rest in a wedge-shaped manner against the interior wall of the cap 3. In the receiving region there is a catch 27 that projects into the slot 26 of one tab 54. The catch is activated by way of a lever 28 that is activated by the press key 8.

Figure 15:
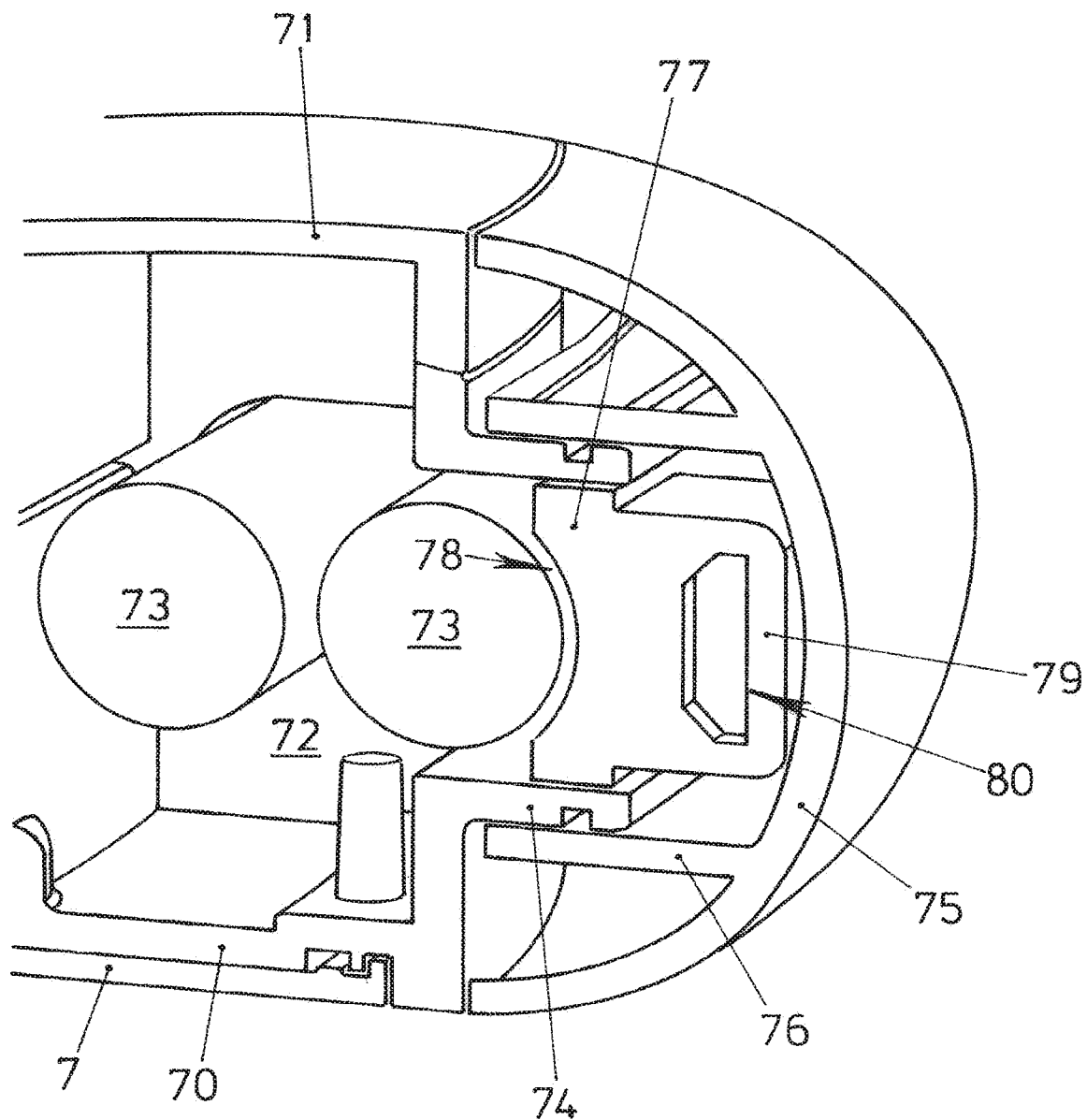
FIG. 15 shows a section of the battery compartment of the device.

As shown in FIG. 15, the housing of the device 1 comprises two half shells 70, 71 that are put together to form a closed housing, whereby the bottom region of the housing is essentially formed by an edge section of one of the half shells 70. In this edge, access to a compartment 72 is provided, into which rechargeable batteries 73 are inserted. The compartment 72 is formed by a circumferential web 74 on the edge section of the half shell 70. In the compartment 72, the batteries 73 are situated side-by-side and antiparallel to each other.

A half-shell-shaped housing cover 75 covers the compartment 72. For this purpose, said housing cover 75 on its inner side also comprises a circumferential counter-web 76 which is fixed onto the web 74 on the half shell 70. In this arrangement, the outside contour of the housing cover 75 is shaped in such a manner that a smooth transition to the outer contours of the half shells 70, 71 is formed.

In the compartment 72 itself, a compartment cover 77 is also provided that rests against the batteries 73 and for this purpose on its inner side comprises a trough-shaped indentation 78 and which on its outer side comprises a recess that forms a connector casing 79. The connector casing 79 rests against the inner side of the housing cover 75 so that in this manner a retaining force is exerted on the batteries 73 when the housing cover 75 with its counter-web 76 is fixed onto the circumferential web 74.

The connector casing 79 is hollow and is open towards the underside of the compartment cover 77. On one wall of the connector casing 79 there is a housing opening 80. A connector board (not shown in the drawing) with a USB connector socket is inserted in the connector casing 79 in such a manner that the opening for the connector is situated in front of the housing opening 80.

Figure 16:
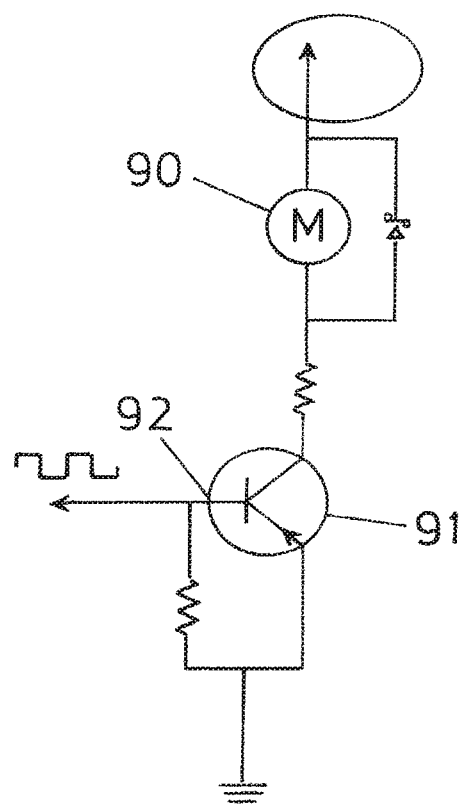
FIG. 16 shows a circuit for controlling a vibrator motor.

As can be derived from FIG. 16, the drive 90 of a vibrator is connected in series with the collector/emitter/path of a transistor 91. A control voltage is applied to the base 92 of the transistor 91. If this control voltage is present, the transistor connects through, and consequently current flows through the motor. If no voltage is present at the base 92, the transistor 91 blocks, and consequently the drive 90 is switched off.

The switching voltage at the base is supplied by a control circuit which by means of a detector detects whether a current flows to the second electrode.

LIST OF REFERENCE NUMBERS

1 Device
2 Base
3 Cap
3a Cap
3b Cap
4 Compartment

5 Button
6 Display
7 First electrode
8 Press key
9 Cap
10 Tongue
11 Tongue
12 Base of a cap
13 Platform
14 Ribs
15 Vibrator
16 Electric motor
17 Cam
18 Pin
19 Pin
20 Second electrode
21 Counter-pin
22 Counter-pin
23 Spring
24 Spring
25 Shoulder
26 Slot
27 Catch
28 Lever
29 Changeover switch
30 Power source
31 Control device
32 Recess
40 Device
41 Housing
50 Bottom
51 Chamber
52a Arm
52b Arm
53 Tab
54 Tab
55 Rubber seal
56 Retaining pin
57 Sealing sheet
58 Soldering lug
59 Step
60 Pillar
61 Channel
62 Retaining bush
63 Head
64 Indentation
65 Connector socket
70 Half shell
71 Half shell
72 Compartment
73 Batteries
74 Web
75 Housing cover
76 Counter-web
77 Compartment cover
78 Indentation
79 Connector casing
80 Housing opening
90 Drive
91 Transistor
92 Base

What is claimed is:
1. A hand-held device for electrically powered skin treatment, comprising:
a housing (41) which is adapted to be grasped by a hand of a user;
a first outer electrode (7) which is adapted to be in contact with the hand of the user when the device is held in the hand of the user for use, wherein the first outer electrode (7) is disposed on the housing (41);
a second outer electrode (20) disposed on a side of the housing and wherein the second outer electrode is placeable on an area of skin to be treated;
an electrical energy source, wherein poles of the electrical energy source are electrically connected to the first and the second electrodes (7, 20) during operation of the device and wherein the electrical energy source is disposed in the housing (41); and
an electrically operated vibrator (15), wherein the electrically operated vibrator (15) is fixed by a socket on a side wall of the housing (41) and is adapted to vibrate the side wall of the housing (41) together with the second outer electrode (20) when operated so that during operation of the device, the device produces an intensified massaging effect on the area of skin to be treated, whereby pores of the skin are widened;
wherein the housing (41) is a shallow housing having an underside formed by a lower wall of the housing and an upper side;
wherein the second outer electrode (20) is disposed on the underside of the housing and extends along almost an entire length of the underside;
wherein the first outer electrode (7) is disposed peripherally on an outer edge of the upper side of the housing (41); and
wherein a display (6) and a button (5) for selecting a treatment program are disposed on the upper side.
2. The device according to claim 1, wherein the electrically operated vibrator (15) comprises an electric motor (16) and a cam (17) fastened to a shaft of the electric motor.
3. The device according to claim 1, further comprising a switching device disposed in the housing (41), wherein the switching device is adjustable by the user and provides a respective electrical connection between the electrical energy source and the first outer electrode (7) and the second outer electrode (20), and wherein the electrically operated vibrator (15) is connected to the electrical energy source by the switching device.
4. The device according to claim 3, wherein the switching device has an electronic memory, wherein parameters of operating states to be selected are stored in the electronic memory, wherein the parameters are selectable by the user by the button (5), and wherein the electrically operated vibrator (15) operates independently of a polarity of an applied voltage.
5. The device according to claim 1, further comprising a current detecting device, wherein the current detecting device detects a current flow through the second outer electrode, a switch in a connection of a drive of the electrically operated vibrator, and a control device, wherein the control device controls the switch such that the switch is only closed when a current flows through the second outer electrode.
6. The device according to claim 1, wherein the electrical energy source is rechargeable batteries, wherein the rechargeable batteries are disposed in a compartment (72), wherein the compartment is covered by a shell-like housing cover (75) whose outside forms a section of an exterior area of the housing (41), wherein the compartment is covered by a removable compartment cover (77) whose inner side is directed toward the batteries (73) and on whose outer side there is disposed a connector socket with at least two poles, and wherein the compartment cover (77) is disposed within the housing cover (75).

7. The device according to claim 6, wherein the connector socket is a USB connector socket.

\* \* \* \* \*